(12) United States Patent
White, IV et al.

(10) Patent No.: US 8,803,693 B2
(45) Date of Patent: Aug. 12, 2014

(54) METHOD AND SYSTEM FOR ALERTING DRIVERS

(75) Inventors: William T. White, IV, Decatur, GA (US); Inga R. Harmon-Cunningham, Stone Mountain, GA (US)

(73) Assignee: Safety First Solutions, Macon, GA (US)

( * ) Notice: Subject to any disclaimer, the term of this patent is extended or adjusted under 35 U.S.C. 154(b) by 98 days.

(21) Appl. No.: 13/364,873

(22) Filed: Feb. 2, 2012

(65) Prior Publication Data

US 2012/0200414 A1 Aug. 9, 2012

Related U.S. Application Data

(60) Provisional application No. 61/439,701, filed on Feb. 4, 2011.

(51) Int. Cl.
*G08B 23/00* (2006.01)
*G08B 21/06* (2006.01)
*B60K 28/06* (2006.01)

(52) U.S. Cl.
CPC .............. *G08B 21/06* (2013.01); *B60K 28/066* (2013.01)
USPC .......................................... 340/575; 340/576

(58) Field of Classification Search
USPC ................... 340/575, 576, 439, 329; 180/272
See application file for complete search history.

(56) References Cited

U.S. PATENT DOCUMENTS

| | | | | |
|---|---|---|---|---|
| 5,684,462 A * | 11/1997 | Gold | ............................. | 340/576 |
| 5,847,648 A * | 12/1998 | Savor et al. | ................... | 340/329 |
| 5,952,928 A * | 9/1999 | Washington et al. | ......... | 340/575 |
| 6,426,702 B1 * | 7/2002 | Young et al. | .................. | 340/576 |
| 6,661,345 B1 * | 12/2003 | Bevan et al. | .................. | 340/575 |

* cited by examiner

*Primary Examiner* — John A Tweel, Jr.

(57) ABSTRACT

Methods and systems in accordance with the present invention provide an alerting alarm system designed to keep drowsy or otherwise inattentive drivers safe while driving. The system comprises an electronic device which comprises an ON/OFF switch, a reset button, a power source; for example a battery housing; a cover, a sound producing member, and a speaker. In some implementations, the device may be permanently affixed within the passenger compartment of a car. In other implementations, the device may be detachably affixed within the passenger compartment of a car. In still further implementations, the device may be free standing, and placed wherever the user desires without being affixed to anything.

19 Claims, 5 Drawing Sheets

METHOD AND SYSTEM FOR ALERTING DRIVERS

This application claims the benefit of provisional application No. 61/439,701 filed Feb. 4, 2011, which is incorporated herein by reference in its entirety.

This generally relates to alerting alarm systems and more specifically to devices used to keep people alert and attentive while they are operating a motor vehicle.

BACKGROUND

Tiredness and fatigue while driving are well-known problems which cause an untold number of traffic accidents, injuries, and even fatalities. Often, drivers will continue to drive despite a clear need for sleep. They may be close to their destination, loathe to lose time by stopping for a nap, or simply reckless. Whatever the reasons, sleepy driving is a known phenomenon which causes vast harm on the roadways.

Conventional alerting alarm systems help sleepy drivers remain alert and attentive, but often suffer shortcomings. Some conventional systems require a driver to constantly maintain a grip on the steering wheel to prevent activation of an alarm. This requirement, which never allows the driver to relax the driver's fingers, may cause discomfort for the driver as well as promoting carpal tunnel syndrome.

Other conventional systems emit a loud and/or shrill beeping noise at regular intervals, designed to keep the driver alert. However, drivers often become used to the metronomic beeping of the device at regular intervals, and this repeated, predictable beeping may become ineffective or even cause the driver to become more sleepy.

Accordingly, there is a desire for a solution to these and other related problems.

SUMMARY OF THE INVENTION

The present invention provides methods and systems for use by a driver of a motor vehicle for keeping the driver alert while driving.

One embodiment, among others, is a method comprising the following steps: producing a response soliciting beep sound to solicit a response from the driver; monitoring a reset switch for the driver response; producing one or more alert beep sounds when the reset switch is not actuated within a predefined time period; and terminating the producing of the one or more alert beep sounds when the reset switch is actuated.

Another embodiment, among others, is a system comprising the following: means for producing a series of response soliciting beep sounds at variable time intervals for soliciting respective responses from the driver; means for resetting commencement of the response soliciting beep sounds, wherein the resetting means is capable of being actuated by the driver; means for producing one or more alert beep sounds commencing at a predefined time period after production of one of the response soliciting beep sounds when the resetting means is not actuated by the driver; and means for refraining from producing the one or more alert beep sounds when the resetting means is actuated by the driver.

Other systems, methods, apparatus, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Methods and systems in accordance with the present invention provide an alerting alarm system designed to keep drowsy or otherwise inattentive drivers safe while driving. The system comprises an electronic device which comprises an ON/OFF switch, a reset button, a power source; for example a battery housing; a cover, a sound producing member, and a speaker. In some implementations, the device may be permanently affixed within the passenger compartment of a car. In other implementations, the device may be detachably affixed within the passenger compartment of a car. In still further implementations, the device may be free standing, and placed wherever the user desires without being affixed to anything.

The device may beep at variable intervals. In some implementations, the variation will be determined by the device, and the device may beep variably without any user input. In other implementations, the user may set the variance of the beeping. Random interval beeping prevents a user from acclimating, or "getting used to" the beeping, as they would if it occurred at a fixed interval, forcing the user to remain more alert.

Further, the device may beep at varying decibel levels. In some implementations, the volume of the beep may increase each time the user does not respond appropriately, for example by depressing the reset button. In other implementations, the volume of the beep may vary randomly. Varying the volume of the beep also prevents a user from acclimating to a single volume, and contributes to the user's continued alertness.

Figure 1:
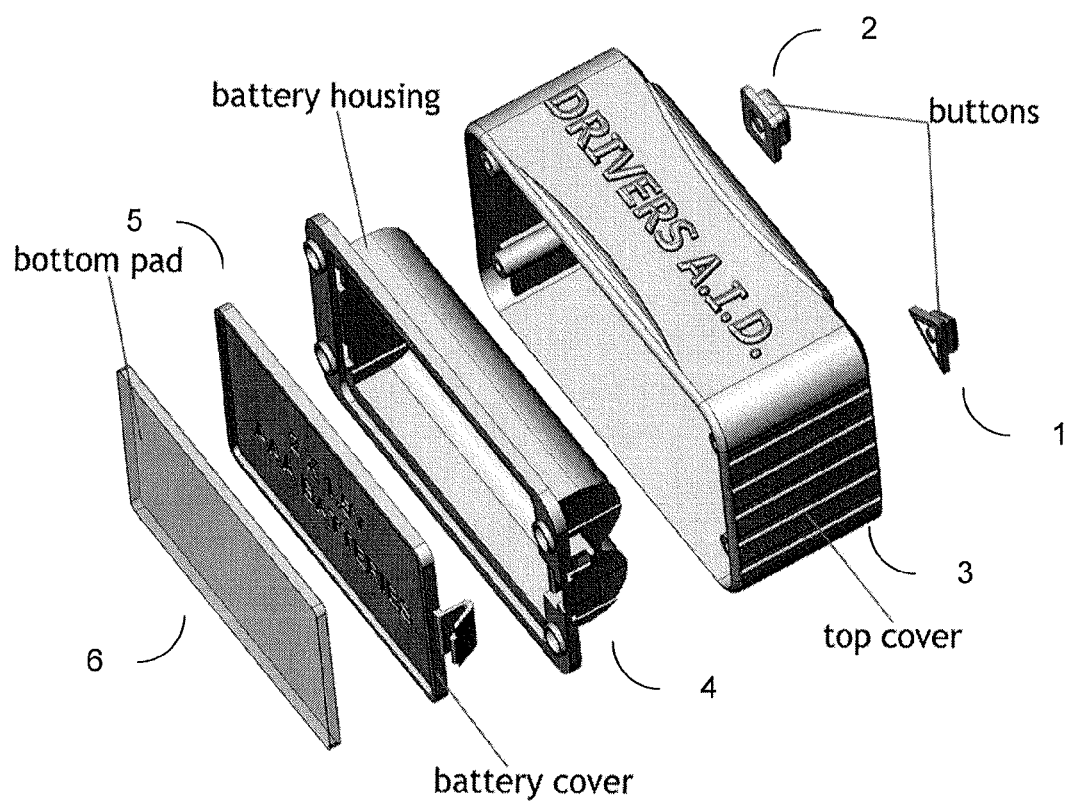
FIG. 1 illustrates an exploded perspective view of an exemplary embodiment of a driver alerting alarm system in accordance with methods and systems consistent with the present invention.

FIG. 1 illustrates an exploded perspective view of an exemplary embodiment of a driver alerting alarm system in accordance with methods and systems consistent with the present invention. ON/OFF Button 1 and Reset Button 2 may be located anywhere on the housing of the device. ON/OFF Button 1 may be depressed to turn the driver alerting alarm device on or off. Reset Button 2 may be depressed to respond to one of the varying alerts emitted by the device. This depression of Reset Button 2 acts to signal to the device that the user is alert. The device further comprises Speaker 3, through which the beeps or other alerting noises created by the device are emitted. The device further comprises Battery Housing 4, which houses the battery that powers the device. In other implementations, the device may be powered by a source other than a battery, for example a power cord that plugs into a motor vehicle's cigarette lighter or other power outlet. In some implementations the device may be powered by 2 AAA batteries. In other implementations, it may be powered by other sized batteries. The device further comprises Battery Cover 5, a cover for Battery Housing 4 which holds the batteries in place within Battery Housing 4. Finally, the device may further comprise Bottom Pad 6, a protective pad which may serve the dual purpose of protecting the device from damage and protecting the surfaces within the passenger compartment of the motor vehicle from damage when the device is mounted or otherwise laid to rest inside the passenger compartment.

Figure 2:
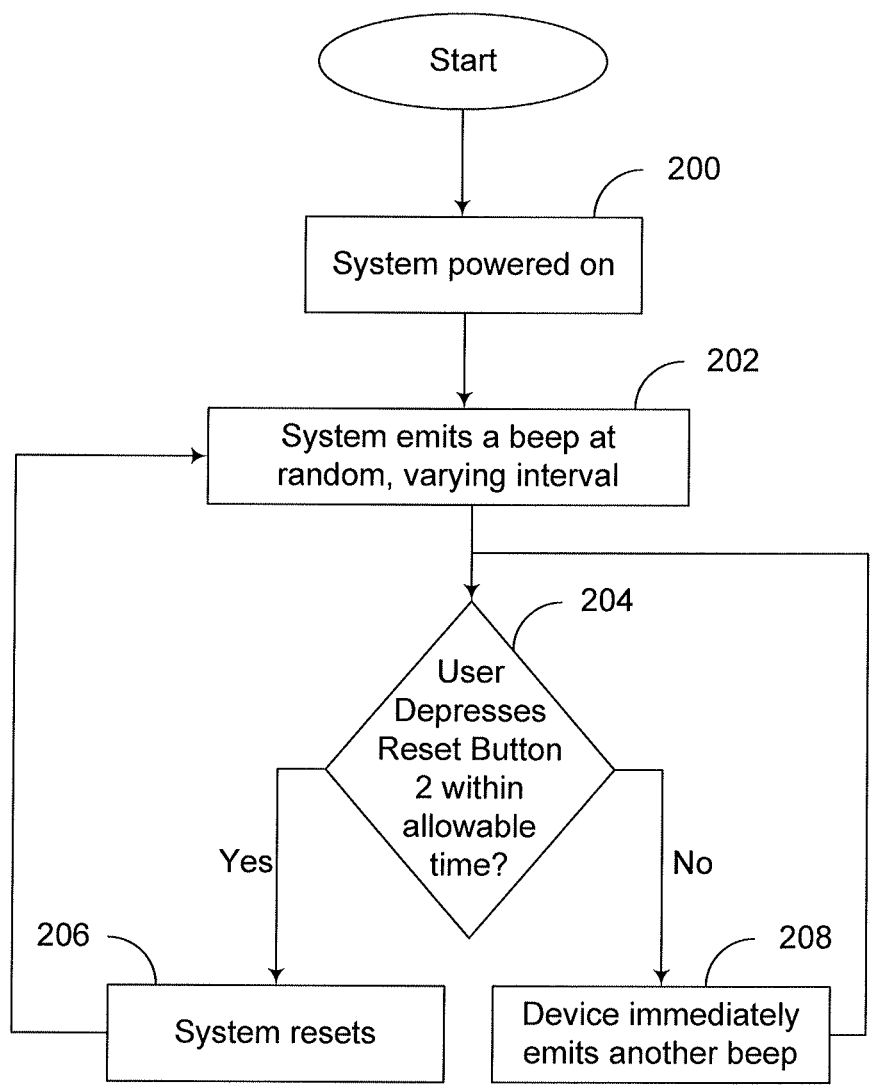
FIG. 2 illustrates steps in an exemplary method of using a driver alerting alarm system in accordance with methods and systems consistent with the present invention.

FIG. 2 illustrates steps in an exemplary method of using a driver alerting alarm system in accordance with methods and systems consistent with the present invention. ON/OFF Button 1 may be depressed to power the alerting alarm system on when the user wishes to use it (step 200). In some implementations, the alerting alarm system is activated immediately upon the user turning the device on. When the alerting alarm system is activated, the varying time interval beeping of the alerting alarm system begins, and the system emits a beep at random, varying intervals determined by the system (step 202). This allows the device to randomly emit an alert sound based on an internal cycle that fluctuates over a randomly determined time interval. In some implementations, this interval may vary between 2 and 14 seconds. However, any other time interval may be used. In some implementations, the variance is generated randomly by the system. In other implementations, the variance may be factory set or set by the user. In other implementations, the variance amount may be a combination of user-defined and device defined variances. Alternatively, the device may also allow the user to choose the time variance between being user-defined and device defined, for example, through a switch (not shown). Reset Button 2 may be depressed in response to the variable beeping of the device. When the device beeps, it is programmed to require a response, in the form of depression of Reset Button 2, within a fixed time interval. In some implementations, this allowable response time may be 2 seconds. If the user depresses Reset Button 2 within the allowable time interval after the beep, the system resets (step 206) and emits another random beep at a varied time interval, repeating step 202. If the user does not respond to the initial beep by depressing Reset Button 2 within the allowable time interval, the device emits another beep immediately upon expiration of the time allotted for the user to depress Reset Button 2 (step 208). In some implementations, this beep may be louder than the initial beep.

Again, the system is programmed to require a response to this second beep, in the form of depression of Reset Button 2, within the fixed allowable response time (step 204), and again, the user may depress Reset Button 2 in response to the beep, thereby resetting the system (step 206). If the user again fails to depress Reset Button 2 within the allowable time interval, the device immediately emits another beep (step 208). In some implementations, this beep may be still louder than the second beep.

This cycle may continue, with regularly spaced, increasingly loud beeps, until the user depresses Reset Button 2 in response to the beeping and resets the system, which then restarts the cycle of time varying beep intervals. It should be understood that the process described above may be discontinued at any time by depressing ON/OFF Button 1, powering off the device.

Figure 3:
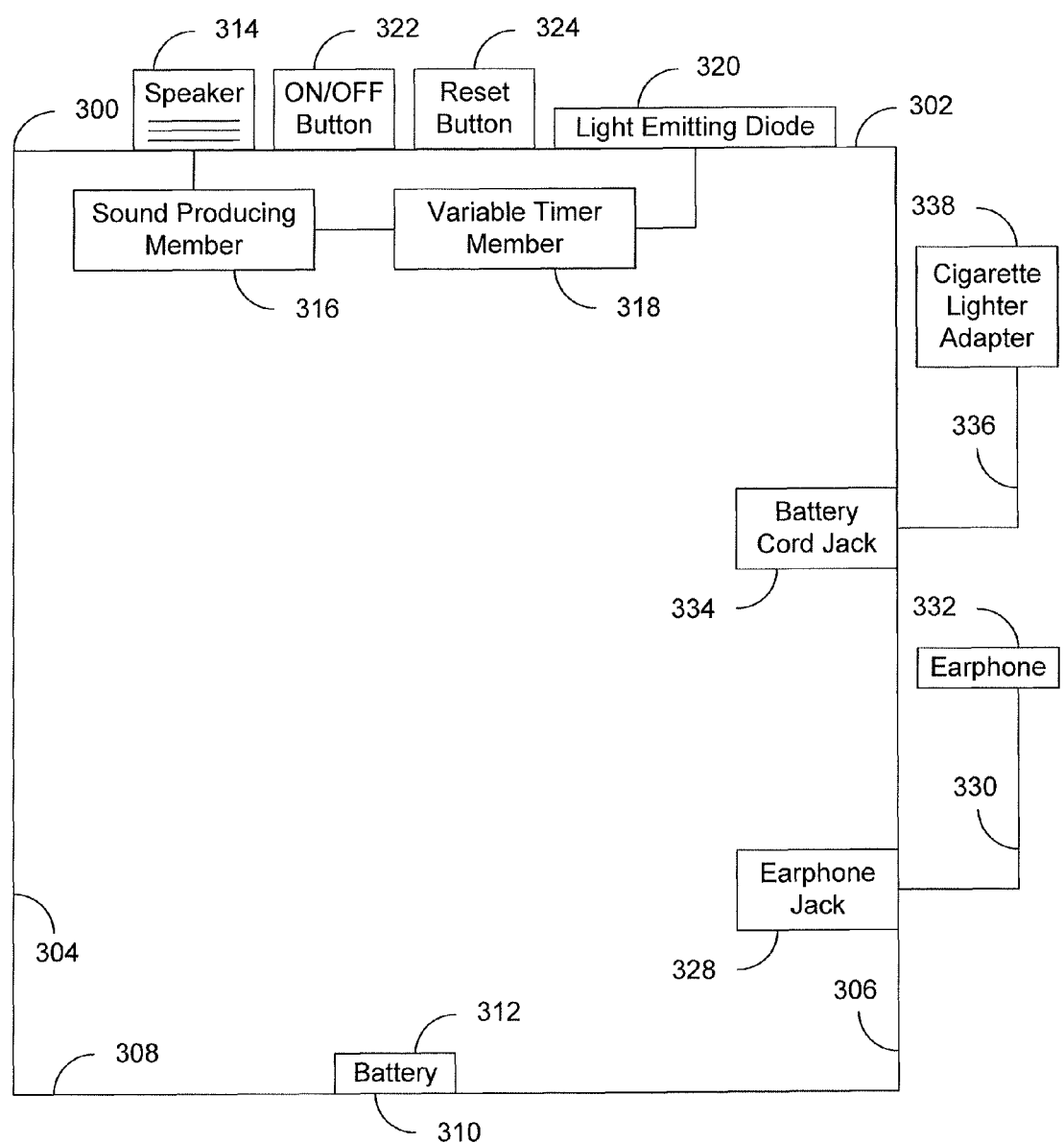
FIG. 3 depicts another exemplary embodiment of a driver alerting alarm system in accordance with methods and systems consistent with the present invention.

FIG. 3 depicts an exemplary embodiment of a driver alerting alarm system in accordance with methods and systems consistent with the present invention. Housing 300 is a housing which encases some parts of the driver alerting alarm system, while other parts are attached thereto. It should be understood that Housing 300 may be any regular or irregular shape. In the embodiment depicted, Housing 300 is in the shape of a rectangle, with End Wall 302, Side Wall 304, Side Wall 306, and End Wall 308. Exemplary dimensions for the housing may be 2.52 inches by 1.39 inches by 0.98 inches. On or within Housing 300 resides Cover 310, which covers Battery 312, and may be opened and closed as needed whenever a user desires to expose Battery 312, for example to replace it. Speaker 314 emits the sounds produced by the device, the device producing such sounds using Sound Producing Member 316. Variable Timer Member 318 is in communication with sound producing member 316, allowing it to produce the various beeps at the appropriate times as discussed above in relation to FIG. 2. Variable Timer Member 318 is also in communication with Light Emitting Diode 320, allowing Light Emitting Diode 320 to illuminate whenever Variable Timer Member 318 signals Sound Producing Member 316 to emit a beep. In some implementations, Variable Timer Member 318 may be a processor or circuit board programmed to include variable time intervals and programmed to activate Sound Producing Member 316 and Light Emitting Diode 320 after the variable time intervals.

The device may further comprise ON/OFF Button 322, which may be depressed or otherwise switched in order to turn the device's power source on or off. Reset Button 324 may be depressed to reset the variably timed beeping cycle of the driver alerting alarm system.

In one implementation, the device may further comprise Earphone Jack 328, which allows an earphone to be plugged into the system. When Earphone Cord 330 is plugged into Earphone Jack 328, the beeps produced by the sound producing member may be directed through Earphone Cord 330 and be audible through Earphone 332.

Finally, the device may further comprise Battery Cord Jack 334, which may allow the device to draw from an alternate power source and/or allow the device's battery to be charged. For example, if Battery Charge Cord 336, attached to Cigarette Lighter Adapter 338, is plugged into Battery Cord Jack 334, and Cigarette Lighter Adapter 338 is plugged into a motor vehicle's cigarette lighter, the device may draw power and/or charge Battery 312 from the motor vehicle battery, thereby saving its own Battery 312 charge to be used when another power source is not available to draw power from. The Battery Charge Cord may be attached directly to a power source other than a Cigarette Lighter Adapter 338, which is optional.

The following is a listing of exemplary internal components within an exemplary driver alert system.

| # | Component | Specification | QTY |
|---|---|---|---|
| 1 | PCB | PCB 60.5 * 28.3 * 1.0MM | 1 |
| 2 | IC | S08 | 1 |
| 3 | triode | 8050D | 1 |
| 4 | buzzer | Dia 12 mm 16 ohm | 1 |
| 5 | LED | 3 mm | 1 |
| 6 | switch | 6 * 6 * 5 | 2 |
| 7 | Electrolytic capacitor | 100 uF +/− 20% IOY | 1 |
| 8 | Surface mounted | 1K ohm 1206 | 1 |

| # | Component | Specification | QTY |
|---|---|---|---|
| 9 | Resistor | 0 ohm 0805 | 1 |
| 10 | Multi-Layer Ceramic Capacitor | 0.1 uF 0603 | 1 |
| 11 | Wires | #30 50 mm | 1 |
| 12 | Wires | #30 50 mm | 1 |
| 13 | Wires | #30 50 mm | 1 |
| 14 | Wires | #30 50 mm | 1 |
| 15 | Wires | #30 50 mm | 1 |

Figure 4:
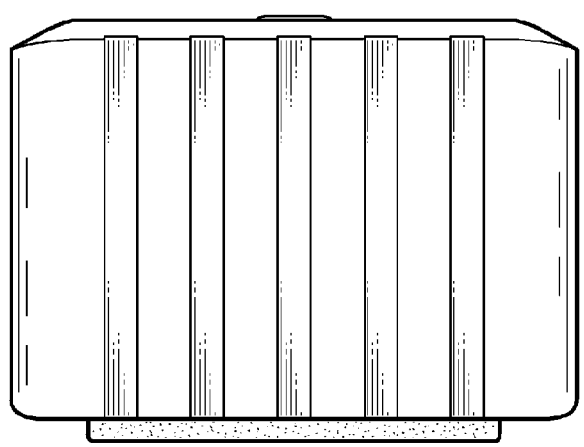
FIGS. 4-6 depict pictures of an exemplary driver alarm system device in accordance with methods and systems consistent with the present invention.
Figure 5:
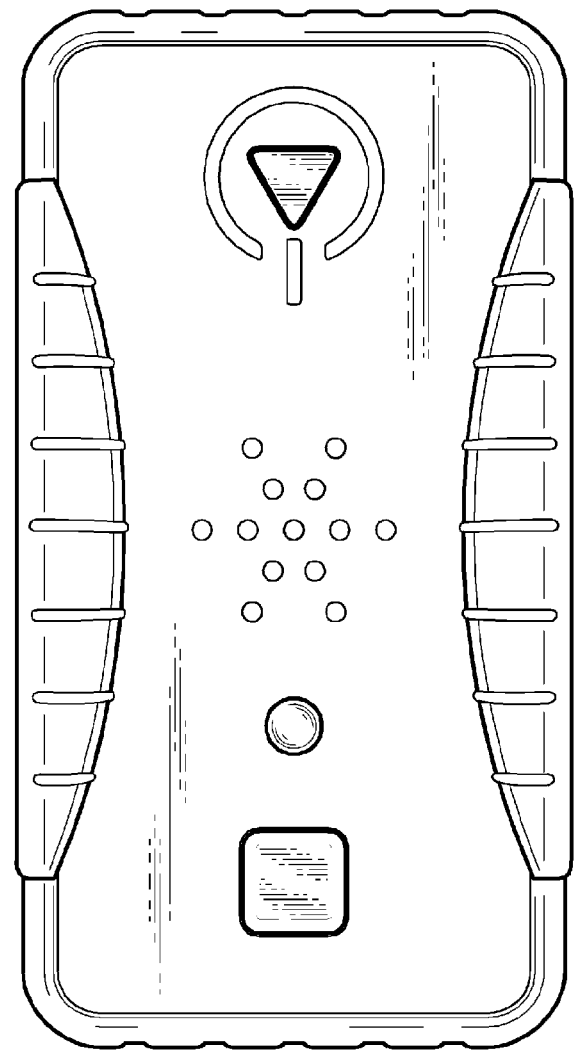
Figure 6:
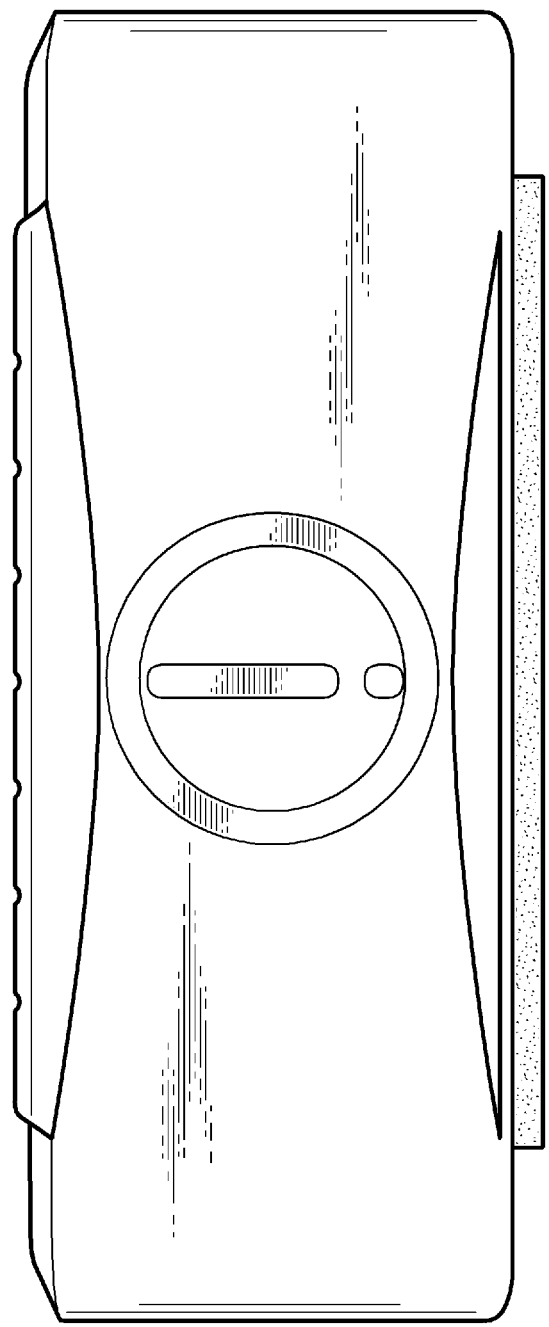

FIGS. 4-6 depict pictures of an exemplary driver alarm system device in accordance with methods and systems consistent with the present invention.

The foregoing description of various embodiments provides illustration and description, but is not intended to be exhaustive or to limit the invention to the precise form disclosed. Modifications and variations are possible in light of the above teachings or may be acquired from practice in accordance with the present invention. It is to be understood that the invention is intended to cover various modifications and equivalent arrangements.

At least the following is claimed:

1. A method for use by a driver of a motor vehicle for keeping the driver alert while driving, comprising:
   producing a response soliciting beep sound to solicit a response from the driver;
   monitoring a reset switch for the driver response;
   producing a series of alert beep sounds at regularly spaced intervals when the reset switch is not actuated within a predefined time period following the response soliciting beep sound; and
   terminating the producing of the series of alert beep sounds when the reset switch is actuated.

2. The method of claim 1, wherein the series of alert beep sounds have a different volume than the response soliciting beep sound.

3. The method of claim 2, wherein the different volume is higher.

4. The method of claim 1, further comprising:
   producing another response soliciting beep sound at a time after terminating the producing of the series of alert beep sounds;
   producing another series of alert beep sounds at the regularly spaced intervals when the reset switch is not actuated within the predefined time period following the another response soliciting beep sound; and
   terminating the other series of alert beep sounds when the reset switch is actuated.

5. The method of claim 4, wherein the time is randomly selected.

6. The method of claim 4, wherein the time is set by the driver.

7. A system for use by a driver of a motor vehicle for keeping the driver alert while driving, comprising:
   means for producing a series of response soliciting beep sounds at variable time intervals for soliciting respective responses from the driver;
   means for resetting commencement of the response soliciting beep sounds, wherein the resetting means is capable of being actuated by the driver;
   means for producing a plurality of alert beep sounds commencing at a predefined time period after production of one of the response soliciting beep sounds when the resetting means is not actuated by the driver, a first alert beep sound of the plurality of alert beep sounds being spaced from a second alert beep sound of the plurality of alert beep sounds by the predefined time period; and
   means for refraining from producing the plurality of the alert beep sounds when the resetting means is actuated by the driver.

8. The system of claim 7, wherein the plurality of alert beep sounds exhibit a different volume than the response soliciting beep sounds.

9. The system of claim 8, wherein the different volume is higher.

10. The system of claim 8, wherein successive alert beep sounds are increasingly louder.

11. The system of claim 7, wherein the variable time intervals are set randomly.

12. The system of claim 7, wherein the variable time intervals are set by the driver.

13. The system of claim 7, further comprising a means for enabling and disabling the producing of the series of response soliciting beep sounds.

14. A system for use by a driver of a motor vehicle for keeping the driver alert while driving, comprising:
   means for producing a response soliciting beep sound to solicit a response from the driver;
   means for monitoring a reset switch for the driver response;
   means for producing a plurality of alert beep sounds at regularly spaced intervals when the reset switch is not actuated within a predefined time period following the response soliciting beep sound; and
   means for terminating the producing of the plurality of alert beep sounds when the reset switch is actuated.

15. The system of claim 14, wherein the plurality of alert beep sounds have a different volume than the response soliciting beep sound.

16. The system of claim 15, wherein the different volume is higher.

17. The system of claim 14, further comprising:
   means for producing another response soliciting beep sound at a time after the terminating means terminates the producing of the one or more alert beep sounds;
   means for producing another plurality of alert beep sounds when the reset switch is not actuated within the predefined time period following the another response soliciting beep sound; and
   means for terminating the producing of the other plurality of alert beep sounds when the reset switch is actuated.

18. The system of claim 17, wherein the time is randomly selected.

19. The system of claim 17, wherein the time is set by the driver.

* * * * *